United States Patent [19]

Chelen

[11] Patent Number: 5,120,739

[45] Date of Patent: * Jun. 9, 1992

[54] METHOD OF TREATING MOTION SICKNESS

[76] Inventor: William Chelen, 4396 Laclamen Dr., Centerville, Ohio 45459

[*] Notice: The portion of the term of this patent subsequent to Feb. 12, 2008 has been disclaimed.

[21] Appl. No.: 618,739

[22] Filed: Nov. 27, 1990

Related U.S. Application Data

[63] Continuation of Ser. No. 491,731, Mar. 12, 1990, Pat. No. 4,992,443.

[51] Int. Cl.$^5$ ............................................. A61K 31/505
[52] U.S. Cl. ...................................................... 514/256
[58] Field of Search ......................................... 514/256

*Primary Examiner*—S. J. Friedman
*Attorney, Agent, or Firm*—Larson and Taylor

[57] ABSTRACT

Certain anticonvulsant drugs have been found to be effective in the treatment of motion sickness. These compounds have the structure:

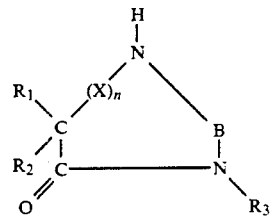

wherein
$R_1$, $R_2$ and $R_3$ are H, aliphatic or aromatic groups;
B is —C=O or —CH$_2$—;
n is 0 or 1;
X is

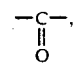

and their non-toxic, pharmaceutically-acceptable acid addition salt.

9 Claims, 2 Drawing Sheets

METHOD OF TREATING MOTION SICKNESS

This application is a continuation of application Ser. No. 07/491,731 filed Mar. 12, 1990, U.S. Pat. No. 4,992,443.

BACKGROUND OF THE INVENTION

This invention relates to the prevention or treatment of motion sickness. More particularly, the present invention is directed to preventing motion sickness by the use of a certain class of anticonvulsants.

Traditional motion sickness therapies rely predominantly upon drugs in the antihistaminic and anticholinergic drugs classes. See Money, K. E., Motion Sickness, *Physiological Reviews,* 1970, 50(1):1-39; Wood, C. D., Graybiel, A., Theory of Antimotion Sickness Drug Mechanisms, *Aerospace Med.,* 1972, 43(3):249-252; and Wood, C. D., Manno, J. E., Wood, M. J., Manno, B. R., Redetzki, H. M., Mechanisms of Antimotion Sickness Drugs, *Aviat. Space Environ. Med.,* 1987. 58(9. Suppl.):A262-5. Examples of such drugs are promethazine, scopolamine, dimenhydrinate and cyclazine. These are sometimes combined with a sympathomimetic agent such as ephedrine or amphetamine to enhance their action and reduce the side effects or lethargy and drowsiness that often accompanies the use of these drugs. Other traditional side effects of drugs presently used in the prevention of motion sickness include blurred vision, dizziness, dry mouth and sedation. In addition, therapy with the present day antimotion sickness drugs whether used alone or in combination with other drugs is less than optimal.

It is an object of the present invention to prevent or treat motion sickness by the use of drugs found to be far more effective than anti-motion sickness agents presently employed without the aforementioned side effects that frequently accompany these drugs.

Another object of the invention is to prevent or treat motion sickness with agents which do not require use of additional enhancing agents or side-effect reducing agents.

SUMMARY OF THE INVENTION

These and other objects are obtained by administering to a patient susceptible to or suffering from motion sickness an anti-motion sickness effective amount of a compound having the structure:

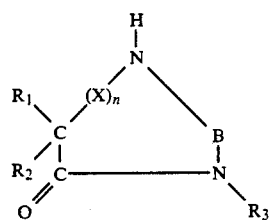

wherein
$R_1$, $R_2$ and $R_3$ are H, aliphatic or aromatic groups;
B is $-C=O$ or $-CH_2-$;
n is O or 1;
X is

and their non-toxic, pharmaceutically-acceptable acid addition salt.

$R_1$, $R_2$ and $R_3$ can be similar or dissimilar and are often a mixture of hydrogen, an aromatic group and an aliphatic group. Suitable aromatic groups for the $R_1$, $R_2$ and $R_3$ groups include aryl groups of 6 to 12 carbon atoms, preferably phenyl. Suitable aliphatic groups for the $R_1$, $R_2$ and $R_3$ groups include alkyl groups of 1 to 5 carbon atoms.

The anti-motion sickness compounds particularly preferred are phenytoin, ethotoin and primidone.

Recent studies of laboratory induced motion sickness in human subjects have revealed novel electroencephalographic changes accompanying the disorder. These EEG changes, similar to those sometimes seen in partial seizure, are characterized by a pattern of high voltage, low frequency (below 1.0 Hertz) oscillations.

The observation of these electroencephalographic changes was coupled with consideration of the symptoms sometimes seen in partial seizure. These symptoms include autonomic dysfunctions like cardiovascular and respiratory irregularities, epigastric sensations and gastrointestinal hypermotility; features nearly synonomous with motion sickness. Consequently, drug treatment with agents in the anticonvulsant class that would stabilize neuronal membranes to excessive stimulation and/or reduce polysynaptic responses seemed indicated. Further investigation led to the discovery that the administration of effective amounts of the above-identified anticonvulsants prevent or alleviate motion sickness.

The term "motion sickness" as used in this specification and appended claims includes airsickness, seasickness, space motion sickness, ground vehicle sickness, e.g., car sickness, flight simulator sickness and earth sickness (the symptoms of motion illness on returning to earth or solid ground after flying in space, water-borne travel, etc.).

DETAILED DESCRIPTION OF THE INVENTION

Figure 1:
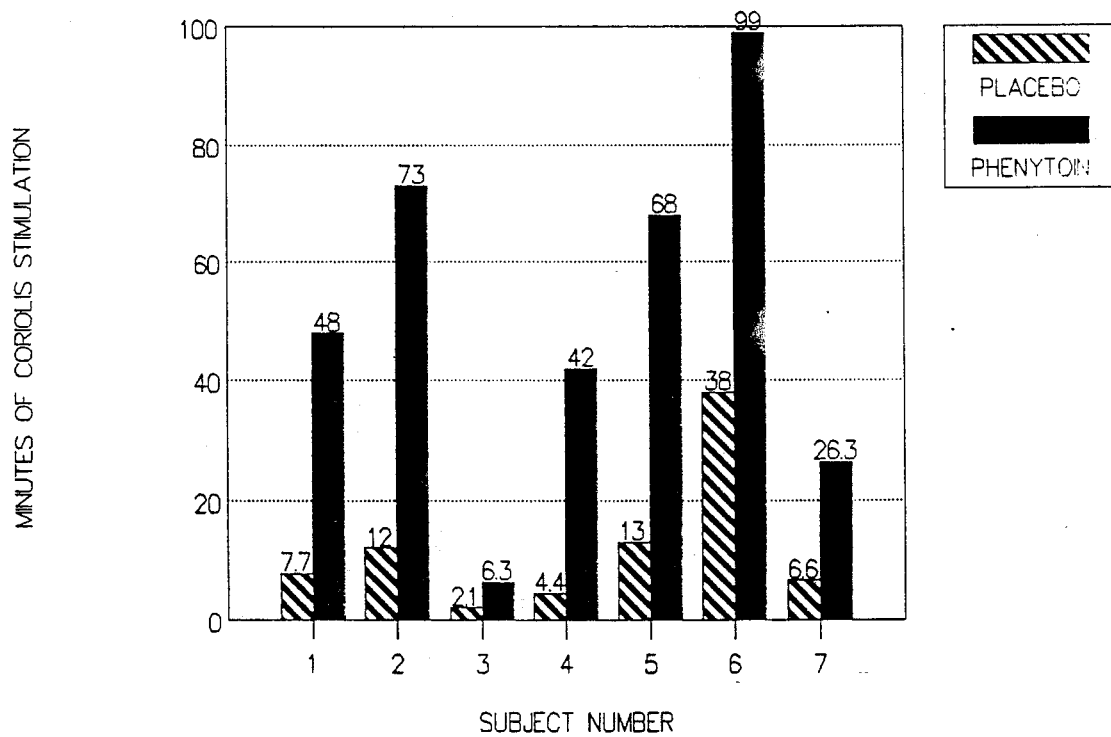

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and ethanesulfonic acid, arylsulfonic acids such as benezenesulfonic acid and p-toluene sulfonic acid and arylcarboxylic acids.

Examples of suitable excipients or pharmaceutical carriers are talc, arabic gum, lactose, starch, magnesium stearate, cacaco butter, aqueous and non-aqueous vehicles, fatty bodies of animal or vegetable origin, paraffinic derivatives, glycols, diverse wetting agents, dispersants or emulsifiers and preservatives.

The active compounds of the invention, singly or in admixture, are administered to a patient susceptible to motion sickness which can be any warm-blooded animal, including man, either before or after the onset of motion sickness symptoms. The administration can be effected orally, intramuscularly or intravenously. The usual daily dosage will depend on the subject treated, the particular compound administered and the method of administration. Generally, the doses used will parallel those used in the treatment of seizures which are dosages that provide a blood level within the range from about 4 to 100 micrograms. For example, for phenytoin, a blood level in the range of about 10 to 20 micrograms per milliliter is satisfactory. The dose necessary to achieve this blood level concentration would be, on average, 1 gram in several divided doses as a loading dose, and 300 milligrams per day thereafter.

The following Example further illustrates the invention but is not to be construed as limiting the invention in any respect.

EXAMPLE

Seven healthy young adult males (25 to 37 years of age) participated. Informed consent was obtained from all subjects.

All subjects' susceptibilities to motion sickness, according to their written responses to motion experience/sickness questionnaires, were unremarkable. All subjects were also, weeks before the formal experiment, evaluated for their response to coriolis stimulation by using the same head motion protocol and rotational speed which would be employed in the trials to follow. Their time course of symptom development and time to nausea during this preliminary evaluation were compared to those recorded during the subsequent placebo trials in order to determine if any adaption was occurring over the course of the trials.

The coriolis motion stimulus was conventionally generated by performing voluntary, random, full range-of-motion right/up, left/up, down/up head motions at ten second intervals while rotating at a constant 14, 16, 18, 20, or 22 rpm in the yaw axis. The rotational rate was chosen with the goal of providing a motion intensity which would induce emesis within approximately 10 to 15 minutes. Increasing individual susceptibility and a corresponding slower rotational rate was subjectively assigned according to an individual's history (frequency and intensity) of car, sea, air, etc. sickness symptomatology reported in the motion experience/sickness questionnaire. More than ten separate physiologic parameters were simultaneously recorded through the experiment. These included respiratory rate and volume, and bipolar temporal and midline electroencephalogram (acquired with subdermal electrodes and amplifiers with a low frequency response extending to 0.2 Hertz).

The subject would regularly report hs subjective symptomatology. Data collection would continue through frank sickness and emesis or until the subject chose to end the experiment.

A double blind placebo controlled crossover experimental technique was employed. At least one week separated each subject's placebo and treatment trials. A total of approximately 1 to 1.4 grams (15 milligrams per kilogram of bodyweight) of phenytoin or placebo, in 5 or 6 equal doses, was taken orally over a 20 hour period prior to the experiment (coriolis stimulation began approximately four hours after the final dose). This dose and schedule was chosen to achieve a blood level in the traditional therapeutic range of 10 to 20 micrograms per milliliter and to obviate any rare side effects associated with acute administration. (Note: In one aborted experiment, a subject reported acute nausea associated with the loading dose administration. This was the specific side effect it was essential to avoid.) A physical examination was performed prior to each experimental trial to characterize balance, reflexes, coordination, performance, as well as nystagmus and any other side effects.

Results

In all trials, physical exam failed to reveal any evidence of neurological symptoms, signs or compromise. Subjects denied the presence of side effects such as double vision, dizziness, tremor, ataxia, nausea, (or as with the more traditional treatment) dry mouth, blurred vision, sedation, etc. Four subjects did, however, report a sense (in fact accurately) that they knew when they had taken the active treatment. Of those four, two reported the sensation of a very slight "light-headedness", and two a sensation of stimulation or alertness.

In each case during the placebo trials, the subject's time to nausea was within ten percent of the time observed in the preliminary coriolis stimulation evaluation. (This implies that adaption was not a significant factor in determining the tolerance to motion in the experimental trials.)

Electroencephalographic changes were also observed in 5 of the 7 subjects in this study. (This is similar to my experience in my prior unpublished preliminary research where 14 of 24 symptomatic untreated subjects developed high voltage temporofrontal delta wave activity.) During the phenytoin trials, this slow wave activity was delayed by several minutes in two subjects compared to their placebo trials. In two other subjects, the electroencephalographic changes were delayed until the onset, after prolonged stimulation, of motion sickness symptomatology. In one of the two subjects who was immune to any motion induced symptomatic response, the electroencephalographic delta wave changes failed to appear.

Tolerance to motion sickness with phenytoin therapy, measured by the number of head motions required to induce emesis, was extended in subject #1 by a factor of 6.2. Subject #2 experienced an extension of tolerance of 6.1 times. Subjects #3, #4 and #7 had extensions of 3.1, 9.5 and 4 times, respectively. Subjects #5 and #6, while reaching emesis with placebo in 13 and 38 minutes respectively, remained asymptomatic for more than an hour during their phenytoin trials before they chose to end the experiments (see FIG. 1).

Figure 2:
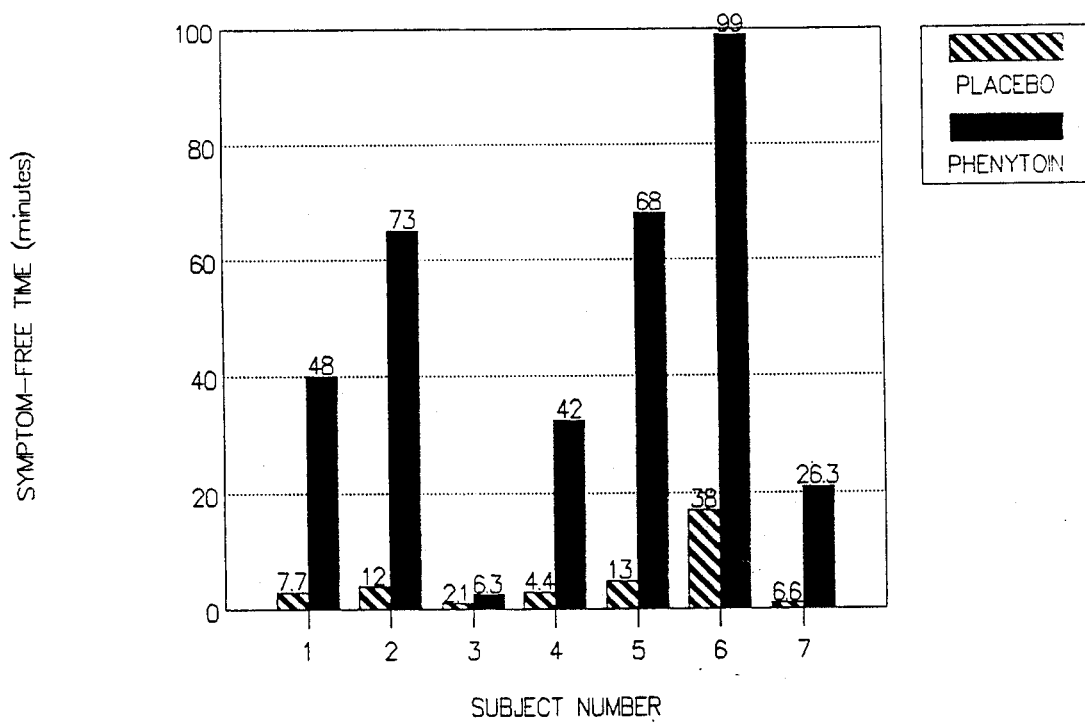

The ratio of the duration of symptom free time with phenytoin versus placebo was even more pronounced. A mean of a factor of 11.9 was obtained (see FIG. 2).

What is claimed is:

1. A method of treating motion sickness comprising administering to a patient susceptible to or suffering from motion sickness, an anti-motion sickness effective amount of a compound having the structure:

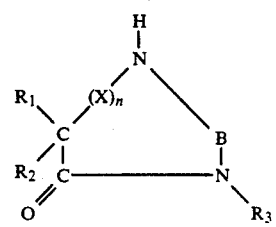

wherein
$R_1$, $R_2$ and $R_3$ are H, aliphatic of 1 to 5 carbon atoms or aryl groups of 6 to 12 carbon atoms;

B is —C=O or —CH$_2$—;

n is 0 or 1;

X is t,100 and their non-toxic, pharmaceutically-acceptable acid addition salt.

2. A method according to claim 1 wherein $R_1$ and $R_2$ are aryl groups.

3. A method according to claim 2 wherein $R_1$ and $R_2$ are phenyl.

4. A method according to claim 1 wherein $R_1$ is an aryl group of 6 to 12 carbon atoms is H.

5. A method according to claim 4 wherein $R_1$ is phenyl.

6. A method according to claim 2 wherein B is —CH$_2$—.

7. A method according to claim 1 wherein $R_3$ is aliphatic.

8. A method according to claim 7 wherein $R_3$ is alkyl.

9. A method according to claim 8 wherein $R_3$ is a lower alkyl of 1 to 5 carbon atoms.

* * * * *